get patent

United States Patent
Di Maio (10) Patent No.: US 11,590,166 B2
(45) Date of Patent: Feb. 28, 2023

(54) COMPOSITION FOR THE TREATMENT OF GASTROINTESTINAL DISORDERS

(71) Applicant: NEILOS S.R.L., Piano di Sorrento (IT)

(72) Inventor: Umberto Di Maio, Piano di Sorrento (IT)

(73) Assignee: NEILOS S.R.L., Piano di Sorrento (IT)

( * ) Notice: Subject to any disclaimer, the term of this patent is extended or adjusted under 35 U.S.C. 154(b) by 538 days.

(21) Appl. No.: 16/479,385

(22) PCT Filed: Jan. 19, 2018

(86) PCT No.: PCT/IB2018/050347
§ 371 (c)(1),
(2) Date: Jul. 19, 2019

(87) PCT Pub. No.: WO2018/134781
PCT Pub. Date: Jul. 26, 2018

(65) Prior Publication Data
US 2019/0374574 A1    Dec. 12, 2019

(30) Foreign Application Priority Data
Jan. 20, 2017   (IT) .................. 102017000006355

(51) Int. Cl.
| *A61K 36/23* | (2006.01) |
| *A61K 33/44* | (2006.01) |
| *A61P 1/12* | (2006.01) |
| *A61K 36/185* | (2006.01) |
| *A61K 38/47* | (2006.01) |
| *A61K 38/48* | (2006.01) |

(52) U.S. Cl.
CPC ............ *A61K 33/44* (2013.01); *A61K 36/185* (2013.01); *A61K 36/23* (2013.01); *A61K 38/47* (2013.01); *A61K 38/4873* (2013.01); *A61P 1/12* (2018.01)

(58) Field of Classification Search
None
See application file for complete search history.

(56) References Cited

U.S. PATENT DOCUMENTS

| 2013/0344145 A1* | 12/2013 | Bernardo Escudero ..................... A61K 31/05 424/465 |
| 2017/0020999 A1* | 1/2017 | Bathaei .................. A61K 31/59 |
| 2018/0338890 A1* | 11/2018 | Glenn, Jr .................. D06L 1/00 |
| 2021/0137857 A1 | 5/2021 | Di Maio |

FOREIGN PATENT DOCUMENTS

| CN | 105394335 | * | 3/2016 |
| CN | 105394335 A | | 3/2016 |
| CN | 105394381 | * | 3/2016 |
| CN | 105394381 A | | 3/2016 |
| WO | 2011/070096 A1 | | 6/2011 |
| WO | WO 2011/070096 | * | 6/2011 |
| WO | 2015/150590 A1 | | 10/2015 |

OTHER PUBLICATIONS

Holtmann, G. et al. A Fixed Combination of Peppermint and Caraway Oil Modulates Postinflammatory Visceral Hyperalgesia. Gastroenterology 126(4)Suppl 2, A640 Apr. 2004. (Year: 2004).*
Niveles Fact Sheet from Tongil about Nivelflatu product, no date available. (Year: 0000).*
Keshavarz et al., "Effects of *Carum carvi* L. (Caraway) extract and essential oil on TNBS-induced colitis in rats," *Research in Pharmaceutical Sciences* 8(1):1-8, Feb. 2013.
Mahady et al., "In Vitro Susceptibility of *Helicobacter pylori* to Botanical Extracts used Traditionally for the Treatment of Gastrointestinal Disorders," *Phytotherapy Research* 19(11):988-991, 2005.
Juwita et al., "Antibacterial activity of papaya leaves (*Carica papaya*,L) infusum against *Escherichia coli*," Indonesian Journal of Medical Microbiology 1( 1) 2012 (English abstract only).
Maznev, "Characteristics of medicinal plants," in Medicinal plants: 15,000 names of medicinal plants, collections and recipes. Description, properties, application, contraindications, Moscow, Lada Commercial and Technical Information Center Ltd., Ripol Classic Publishing House Ltd., Dom XXI Publishing House Ltd., 2006, pp. 914-916.

* cited by examiner

*Primary Examiner* — Ralph J Gitomer
(74) *Attorney, Agent, or Firm* — James S. Keddie; Bozicevic, Field & Francis LLP (57) ABSTRACT

The present invention relates to a pharmaceutical composition which contains activated charcoal, *Carum carvi* extract, papain and, optionally, α-galactosidase and β-galactosidase for the treatment of gastrointestinal disorders.

5 Claims, 3 Drawing Sheets

COMPOSITION FOR THE TREATMENT OF GASTROINTESTINAL DISORDERS

FIELD OF THE INVENTION

The present invention relates to a pharmaceutical composition which contains activated charcoal, *Carum carvi* extract, papain and, if present, α-galactosidase and β-galactosidase, for the treatment of gastrointestinal disorders such as flatulence, meteorism and diarrhoea, and to the use of said composition to modify the rate of gastric emptying and/or for the prevention or elimination of excess gas in the intestine.

The present invention is based on the synergistic action of the aforesaid active ingredients.

DESCRIPTION

Gastrointestinal Disorders

Various disorders affecting the gastrointestinal system, associated with causes of varying nature, are defined as such.

The main gastrointestinal disorders are the following:
Pyrosis;
Dyspepsia;
Aerophagia;
Meteorism;
Flatulence;
Constipation;
Diarrhoea.

Intestinal motility disorders represent an important social problem; in fact, it is well known that unpleasant symptoms such as constipation, flatulence, diarrhoea, etc. affect a large number of people, sometimes to such an extent as to condition their lifestyle (Ng K S, Nassar N, Hamd K, Nagarajah A, Gladman M A. Prevalence of functional bowel disorders and faecal incontinence: an Australian primary care survey. Colorectal Dis. 2015; 17:150). Moreover, there has been a strong statistical increase in serious colon pathologies (diverticulits, polyps, tumours, etc.) which are linked to and dependent on the state of intestinal motility, among other things. It has been estimated that in industrialised countries, about 20% of the population has reported constipation at some point during their lifetime and that constipation increases with age and decreases with increases in body weight (Le Pluart D, Sabaté J M, Bouchoucha M, Hercberg S, Benamouzig R, Julia C. Functional gastrointestinal disorders in 35,447 adults and their association with body mass index. Aliment Pharmacol Ther. 2015; 41:758-67). In underdeveloped countries, by contrast, where good hygienic conditions do not exist, diarrhoea is one of the main causes of death (de Vrese M, Marteau P R. Probiotics and prebiotics: effects on diarrhea. J Nutr. 2007; 137:803S-11S). These problems make suitable studies necessary in order to identify new drugs active on the gastrointestinal tract.

Pyrosis

Pyrosis, also defined as retrosternal pain, is a painful symptom generally localised in proximity to the sternum and associated with gastrointestinal disorders, in particular of the stomach.

Pyrosis can occur spontaneously or as a result of the ingestion of irritating foods or particular drugs.

It is generally associated with reflux, which brings gastric or duodenal material in contact with a dysfunctional oesophagus [W. G. Thompson and K. W. Heaton, "Heartburn and globus in apparently healthy people," Can. Med. Assoc. J., vol. 126, no. 1, pp. 46-48, 1982]. In the absence of demonstrated hiatal hernia or aerophagia, it is to be considered a functional disorder. If the pyrosis is secondary to diseases such as reflux oesophagitis, it generally appears on a daily basis and any factor capable of facilitating reflux, such as, for example, bending forward, causes the disorder to manifest itself. Obstacles to gastric emptying and night time decubitus can increase pyrosis.

Since the main cause of pyrosis is the contact of acid with the oesophageal mucosa, one of the most widely used strategies for the treatment of this disorder is the use of drugs capable of reducing, through various mechanisms of action, acid secretion in the stomach.

Gastric secretion is a process that depends on neural (acetylcholine), paracrine (histamine) and endocrine (gastrin) factors. These factors act on $M_3$, $H_2$, $CCK_2$ receptors, respectively, located principally on the membrane of the gastric parietal cells.

There are three main stimuli responsible for gastric secretion and each one plays a specific role in adapting the entity of secretion to functional requirements:

GASTRIN: protective hormone secreted by the G cells of the gastric antrum; it is the most powerful stimulus to gastric acid secretion. The stimuli that determine its release include the gastrin-releasing peptide, released by enteric nerve endings. Gastrin acts on the parietal cells, chief cells and enterochromaffin-like cells, responsible for the secretion of histamine.

HISTAMINE: binds to the histamine receptors of parietal cells. Histamine, by interacting with the $H_2$ receptor, in synergy with gastrin, stimulates the release of hydrochloric acid and pepsin.

ACETYLCHOLINE: stimulates the parietal cells and chief cells, thereby increasing the secretory activity of the stomach; furthermore, it increases smooth muscle contractions.

One of the mechanisms which intervene in the inhibition of gastric secretion is the action of somatostatin, secreted by the D cells of the gastric antrum, which inhibits gastric secretion. Its release is induced by an intraluminal gastric pH less than 3, which simultaneously suppresses the secretion of gastrin via a negative feedback mechanism.

The secretion of acid by the stomach takes place through the action of the $H^+/K^+$—ATPase proton pump, present in the parietal cells and activated by the cyclic AMP and calcium ion pathway.

The most widely used pharmacological treatments in the case of gastric hyperacidity are the following:

Proton pump inhibitors. After being absorbed, they penetrate the gastric parietal cells and bind covalently with the proton pump (sulphidrilic groups), inactivating them irreversibly. Prolonged use of these drugs is associated with an increase in cardiovascular risk and the risk of developing chronic kidney disease [Y. Xie, B. Bowe, T. Li, H. Xian, S. Balasubramanian, and Z. Al-Aly, "Proton Pump Inhibitors and Risk of Incident CKD and Progression to ESRD.," J. Am. Soc. Nephrol., p. ASN.2015121377-, April 2016].

$H_2$ receptor antagonists. They compete reversibly with histamine to bind with $H_2$ receptors. They are decidedly less potent than pump inhibitors.

Prostaglandin analogues. They induce an effect analogous to the one generated by prostaglandins through their interaction with $EP_3$ receptors, reduce intracellular cyclic AMP and, consequently, gastric acid secretion. Furthermore, $PGE_2$ exerts cytoprotective effects, which include the secretion of mucus and bicarbonate, as well as an increase in the mucosal blood flow through the promotion of nitrogen monoxide production by NOS (nitric oxide synthase), with a consequent vasodilatory effect.

Dyspepsia

It involves a series of symptoms, episodic or persistent, which are felt mainly in the upper portion of the abdomen. It can be associated with a sense of heaviness and anorexia.

It is a rather common gastrointestinal disorder, which is found in a large part of the world population: in the United Kingdom, over 40% of adults have reported at least one episode of dyspepsia in the last 12 months.

Dyspepsia is classified as follows:

Functional or primitive dyspepsia. A disorder of the upper part of the abdomen, of which it is not possible to identify an adequate organic, biochemical or structural cause.

Organic or secondary dyspepsia. It can have different causes, including pathologies such as oesophagitis, gastritis, duodenitis, pancreatitis, and hepatitis, but also food intoxications, the use of narcotic substances or some types of medicines.

There are various pharmacological treatments for this disorder. The main ones are the following:

Drugs with a prokinetic action. They act through various mechanisms of pharmacological action. They lead to an increase in the frequency of movement of the stomach, thus increasing the rate of gastric emptying.

Proton pump inhibitors. As described previously, they inhibit gastric secretion.

Antacids. They react with the hydrochloric acid present in the stomach, increasing the pH of the gastric content and preventing damage to the oesophageal mucosa in the event of reflux.

Biliary acids.

Anxiolytics.

Abdominal Bloating and Meteorism

Abdominal bloating and meteorism are two of the most common gastrointestinal symptoms. These disorders are mainly found in patients with irritable bowel syndrome (IBS): the percentage of patients who suffer from disorders of this type reaches as high as 96% of subjects with IBS [G. F. Longstreth, W. G. Thompson, W. D. Chey, L. A. Houghton, F. Mearin, and R. C. Spiller, "Functional Bowel Disorders," Gastroenterology, vol. 130, no. 5, pp. 1480-1491, April 2006]. The incidence of bloating and meteorism in the normal population is in any case very high and ranges from 20 to 30% [A. K. Tuteja, N. J. Talley, S. K. Joos, K. G. Tolman, and D. H. Hickam, "Abdominal bloating in employed adults: Prevalence, risk factors, and association with other bowel disorders," Am. J. Gastroenterol., vol. 103, no. 5, pp. 1241-1248, May 2008], [N. J. Talley, P. Boyce, and M. Jones, "Identification of distinct upper and lower gastrointestinal symptom groupings in an urban population.," Gut, vol. 42, no. 5, pp. 690-5, May 1998].

These disorders, despite not being particularly serious, tend to reduce the quality of life of the patients who suffer from them. In fact, over 50% of the people with meteorism report a significant impact on their quality of life [R. S. Sandler, W. F. Stewart, J. N. Liberman, J. A. Ricci, and N. L. Zorich, "Abdominal pain, bloating, and diarrhea in the United States: Prevalence and impact," Dig. Dis. Sci., vol. 45, no. 6, pp. 1166-1171, June 2000].

There are numerous causes that lead to the onset of these disorders [A. Foley, R. Burgell, J. S. Barrett, and P. R. Gibson, "Management strategies for abdominal bloating and distension," Gastroenterol. Hepatol., vol. 10, no. 9, pp. 561-571, 2014]. One of the main causes is the production of intestinal gas, which derives from the fermentation of carbohydrates and proteins by intestinal bacterial flora. This leads to an accumulation of intraluminal gas, which causes bloating and abdominal distension. Another possible cause of the accumulation of gas in the intestine is aerophagia, i.e. the ingestion of gas, which generally occurs during meals.

In individuals who suffer from irritable bowel syndrome, another cause of bloating and meteorism could be the accumulation of liquids in the intestinal lumen, caused by the presence of low-molecular weight carbohydrates such as fructose and mannitol, but also of polyols that could be taken in through the diet.

The pharmacological treatments mainly consist in:

changes in the diet, so as to reduce the intake of carbohydrates that could be fermented;

prosecretory and prokinetic agents, such as linaclotide, prucalopride and lubiprostone. Despite being effective, these drugs might improve the problem of intestinal gas accumulation, but worsen the problem of the flatulence, as the episodes of flatulence would inevitably increase;

antidepressants: in this case, not all the evidence suggests therapeutic effectiveness in the treatment of abdominal bloating;

antibiotics: rifaximin, an antibacterial belonging to the rifamycin family, is not absorbed in the intestine and this increases its safety of use. In the clinical studies conducted, however, it has shown only modest effectiveness in reducing intestinal gas;

Probiotics: in the case of flatulence induced by a dysbiosis, the use of probiotics could act on the cause of this disorder. However, an excessive use of probiotics is associated with a worsening of meteorism and flatulence.

Flatulence

Some patients complain of an excessive expulsion of gas through the rectum, which may become a cause of strong social unease.

The physiology and pathophysiology of flatulence have not yet been completely clarified [F. Azpiroz and J. Malagelada, "Abdominal Bloating," Gastroenterology, vol. 129, no. 3, pp. 1060-1078, September 2005]. The expelled gases originate in the colon, where the chemical compounds not absorbed with the diet can be fermented by bacteria. The amount and type of gas produced depend not only on diet, but also on the metabolic activity of colonic microbiota [C. Manichanh, A. Eck, E. Varela, J. Roca, J. C. Clemente, A. González, D. Knights, R. Knight, S. Estrella, C. Hernandez, D. Guyonnet, A. Accarino, J. Santos, J.-R. Malagelada, F. Guarner, and F. Azpiroz, "Anal gas evacuation and colonic microbiota in patients with flatulence: effect of diet," Gut, vol. 63, no. 3, pp. 401-8, 2014]. The main gases produced by bacteria are hydrogen, carbon dioxide and methane, which account for 74% of the volume of the flatus of normal subjects.

In addition to physiological causes, that is, the swallowing of air through the oesophagus and production of gas by the bacterial flora, there also exist psychological and pathological causes of flatulence.

The main psychological cause is stress, which can be correlated to the occurrence of flatulence. The main pathological causes can be an increase in intestinal motility or lowering of the pain threshold due to pathologies such as peptic ulcer, ulcerous rectocolitis, Crohn's disease and diverticulitis.

The main treatments for this disorder are the following:

Changes in diet, with a reduction of carbohydrates and fermentable polyols;

Surfactants, such as simethicone, which should increase the coalescence of gas bubbles in the intestine;
Prokinetics;
Antibiotics;
Bismuth.

Diarrhoea

Diarrhoea is a disorder of defecation characterised by an increase in the emission of a quantity of stools exceeding 200 g daily, with a decrease in their consistency and an increase in the frequency of bowel movements. It can be acute if its duration is less than two weeks, persistent if comprised between two and four weeks and chronic if it has a longer duration.

Acute diarrhoea is mainly triggered by infectious agents (in 70% of the cases), but may also be due to the use of drugs (e.g.: chemotherapeutics), the presence of fecalomas, the reintroduction of solid foods after a period of fasting, radiation and other pathological conditions (diverticulitis, heavy metal intoxication, intestinal ischemia, allergies or intolerances).

There are many microorganisms that can provoke acute diarrhoea; worth mentioning among them are: *Staphylococcus aureus, Escherichia coli, Vibrio cholerae, Clostridium difficile, Campylobacter jejuni, Salmonella* spp., *Shigella* spp., *Giardia lamblia* (or *intestinalis*), *Entamoeba histolytica*, Rotavirus, Adenovirus and several species of helminths. However, the list is extremely long.

Acute diarrhoea due to an infectious cause is a serious problem in developing countries, as it is believed to cause the death of at least 4 million children under age 5 each year. These pathologies find fertile ground for propagation in areas with precarious hygienic and health conditions: lack of safe drinking water, overcrowding, the presence of undisposed waste and inadequate cooking of some foods.

Chronic diarrhoea is generally due to the presence of irritable bowel syndrome, but can also be due to the presence of celiac disease or inflammatory intestinal diseases (Crohn's disease, ulcerous rectocolitis). These may be accompanied by other causes such as: eosinophilic gastroenteritis, radiation, pancreatic failure, lactase deficiency, short bowel syndrome, Whipple's disease, carcinoid syndrome, Zollinger-Ellison syndrome, tumours or endocrine system alterations, fecalomas, and the abuse of laxatives.

The main pharmacological treatments for diarrhoea are the following:
Antibiotics. In some cases, the use of antibiotics may be taken into consideration in the event of persistent diarrhoea in which it has been possible to identify the microorganism responsible. Recourse to antibiotics becomes necessary in people with immunodeficiencies or neoplasmas, or wearers of orthopaedic or vascular prostheses. The use of antibiotics in the treatment of diarrhoea is controversial where the responsible pathogen has not been identified.
Antidiarrhoeals, antimuscarinics and other symptomatic treatments. Their use must be considered with great caution, as they do not act at the level of the causal pathological process. In the case of diarrhoeas of an infectious nature, moreover, they can length the duration of the disease itself, as well as induce complications that may also be serious, such as: intestinal perforation and megacolon. They can be occasionally used in the case of diverticular disease or irritable bowel syndrome. They are in any case products whose use is not recommended in children and the elderly.

The pharmacological therapies like the ones described above inevitably result in side effects, including severe ones, and cannot be tolerated by some individuals or cannot be applied due to concomitant therapies aimed at other disorders or pathologies.

There is thus a felt need to provide a preventive or curative treatment for gastrointestinal disorders, mainly for dyspepsia, pyrosis, meteorism and/or flatulence, which is tolerated by the majority of the individuals affected by such disorders and is fundamentally devoid of side effects.

As a solution to this problem, the present invention provides a composition based on natural substances, as disclosed in the appended claims.

The present invention relates to a composition comprising a mixture which comprises, or, alternatively, consists of at least the following components:
a. activated charcoal,
b. *Carum carvi* extract, and
c. papain for the curative or preventive treatment of gastrointestinal disorders.

The present invention further relates to the use of a composition comprising a mixture which comprises, or, alternatively, consists of
a. activated charcoal,
b. *Carum carvi* extract, and
c. papain to increase the rate of gastric emptying and/or for the prevention of the formation or the elimination of excess gas in the intestine.

Unless otherwise specified, the content of a component in a composition relates to the percentage by weight of that component relative to the total weight of the composition.

Unless otherwise specified, the indication that a composition "comprises" one or more components means that other components can be present in addition to the one or ones specifically named and the indication that a composition "consists" of given components means that the presence of other components is ruled out.

The present invention comprises both the administration of the ingredients specified above in the same composition, i.e. simultaneously, and the administration thereof in sequence, i.e. within a given period of tempo, by way of non-limiting example, within a few minutes to within 3-6 hours, in separate compositions. In the context of the present invention, "gastrointestinal tract" means the part of the digestive apparatus comprised between the oesophagus and the rectum. In particular the present invention is aimed at the treatment of disorders of the oesophagus, stomach and intestine, preferably of the intestine, and the symptoms thereof.

Activated Charcoal

Activated charcoal is a charcoal characterised by the presence of numerous pores which significantly increase the surface extent thereof, enabling the adsorption of chemical compounds. One gram of activated charcoal possesses, in fact, a surface area of 3000 m$^2$ (E. C. Dillon, J. H. Wilton, J. C. Barlow, and W. A. Watson, "Large surface area activated charcoal and the inhibition of aspirin absorption," Ann. Emerg. Med., vol. 18, no. 5, pp. 547-552, 1989).

Activated charcoal is produced from wood, plants or other materials exposed to high temperatures in oxygen-free environments.

Activated charcoal powder, with reference to the Italian Official Pharmacopeia 11th edition, is prepared by pyrolysis of wood pulp and is "activated" through a particular process capable of removing the previously adsorbed substances with a decrease in the particle size and the production of a dense network of pores essential for the adsorption process.

The capacity of activated charcoal to adsorb intestinal gases makes it a valid active ingredient for the treatment of gastrointestinal disorders associated with an excessive production of gas by bacteria. The effectiveness of administering this raw material in reducing intestinal gas has been demonstrated in various clinical studies.

In a multi-centre, randomised, cross-over, double-blind clinical study, the change in the concentration of hydrogen in the expired gas was measured following the ingestion of lactulose as a fermentation substrate (N. K. Jain, V. P. Patel, and C. S. Pitchumoni, "Efficacy of activated charcoal in reducing intestinal gas: a double-blind clinical trial.," July 1986). The healthy volunteers participating in the study (30 in the United States, 69 in India) were treated with a capsule of gelatine (placebo) or with a capsule containing charcoal (260 mg). The participants received 4 capsules of placebo or charcoal, followed by 15 mL of lactulose after 30 minutes, then another 4 capsules 30 minutes after the administration of lactulose. The concentration of hydrogen in the expired air was monitored and different symptoms associated with flatulence were recorded. Compared to the placebo, a significantly lower concentration of hydrogen was found in the group treated with charcoal than in the placebo group ($p<0.05$) (N. K. Jain, V. P. Patel, and C. S. Pitchumoni, "Efficacy of activated charcoal in reducing intestinal gas: a double-blind clinical trial.," July 1986 July; 81(7):532-5).

Another randomised double-blind clinical study was conducted on 10 healthy adult volunteers, to whom capsules with a placebo, capsules with 260 mg of charcoal or capsules with 20 mg of simethicone were administered (N. K. Jain, V. P. Patel, and C. S. Pitchumoni, "Activated charcoal, simethicone, and intestinal gas: A double-blind study," Ann. Intern. Med., vol. 105, no. 1, pp. 61-62, July 1986). The administration scheme again provided for the administration of 4 capsules, followed by the ingestion of 20 mL of lactulose after 30 minutes, and then by the administration of another 4 capsules after 30 minutes. The breath concentration of hydrogen was measured and the symptoms associated with intestinal discomfort were recorded using a specific questionnaire. The activated charcoal reduced the hydrogen concentrations in a statistically significant manner; furthermore, it led to a reduction in the area subtended by the curve that describes the hydrogen concentration in the expired air as a function of time.

The effectiveness of activated charcoal was also demonstrated in another clinical study (R. G. Hall, H. Thompson, and A. Strother, "Effects of orally administered activated charcoal on intestinal gas.," Am. J. Gastroenterol., vol. 75, no. 3, pp. 192-6, March 1981). Three capsules containing activated charcoal (194 mg) or a placebo were administered to the volunteers participating in the study before a "normal" meal (devoid of ingredients known to induce the formation of intestinal gas) or a "gas forming" meal (containing beans) and 3 capsules were administered after the meals. A significant reduction in the episodes of flatulence was found 2 hours after the meal, as well as a reduction in the breath concentration of hydrogen (R. G. Hall, H. Thompson, and A. Strother, "Effects of orally administered activated charcoal on intestinal gas.," Am. J. Gastroenterol., vol. 75, no. 3, pp. 192-6, Mar. 1981).

In the composition of the present invention, the charcoal is preferably of vegetable origin.

Carum Carvi

*Carum carvi*, known as caraway or Persian cumin, is a medicinal plant belonging to the family Apiaceae, widely used in traditional medicine for its various pharmacological properties, which are mainly attributed to the aromatic substances present in the essential oil (R. G. Hall, H. Thompson, and A. Strother, "Effects of orally administered activated charcoal on intestinal gas.," Am. J. Gastroenterol., vol. 75, no. 3, pp. 192-6, March 1981).

The main classes of chemical compounds present in the essential oil of caraway are monoterpene hydrocarbons, oxygenated monoterpenes and oxygenated sesquiterpenes (M. Jalali-Heravi, B. Zekavat, and H. Sereshti, "Use of gas chromatography-mass spectrometry combined with resolution methods to characterize the essential oil components of Iranian cumin and caraway," J. Chromatogr. A, vol. 1143, no. 1-2, pp. 215-226, March 2007), (H. Kallio, K. Kerrola, and P. Alhonmaki, "Carvone and limonene in caraway fruits (*Carum carvi* I) "analyzed by supercritical charcoal-dioxide extraction gas chromatography" J. Agric. Food Chem., vol. 42, no. 11, pp. 2478-2485, November 1994). Fatty acids, aldehydes, ketones and esters are also present. From a number of studies it has emerged that the main chemical compounds of the essential oil of caraway are carvacrol, carvone, α-pinene, limonene, γ-terpinene, linalool, carvenone, and p-cymene (R. G. Hall, H. Thompson, and A. Strother, "Effects of orally administered activated charcoal on intestinal gas.," Am. J. Gastroenterol., vol. 75, no. 3, pp. 192-6, March 1981).

In the aqueous seed extract, on the other hand, there are flavonoids, glycosides, lignins, alkaloids and other phenolic compounds (R. G. Hall, H. Thompson, and A. Strother, "Effects of orally administered activated charcoal on intestinal gas.," Am. J. Gastroenterol., vol. 75, no. 3, pp. 192-6, March 1981).

Caraway has shown various pharmacological activities: antioxidant, prokinetic, antispasmodic, antimicrobial, antitumor, hypoglycaemic, diuretic and immunomodulating activities.

Preferably, but without limitation, in the context of the present invention use is made of dry extract of *Carum carvi* obtained by aqueous extraction of *Carum carvi*, more preferably in a mixture with an excipient, such as maltodextrin, for example in an E/D (Excipient/drug, i.e. plant extract) ratio of 1:4.

The antioxidant activity of the oil and caraway aqueous extract has been demonstrated in various tests (R. G. Hall, H. Thompson, and A. Strother, "Effects of orally administered activated charcoal on intestinal gas.," Am. J. Gastroenterol., vol. 75, no. 3, pp. 192-6, March 1981). The radical-scavenger activity of caraway against DPPH has been demonstrated (A. Najda, J. Dyduch, and N. Brzozowski, "Flavonoid content and antioxidant activity of caraway roots (*Carum carvi* L.).," Veg. Crop. Res. Bull., vol. 68, no. 1, pp. 127-133, January 2008). The antioxidant properties are mainly attributable to monoterpene alcohols, contained in the essential oil, linalool, carvacrol, anetol, estragol and the polyphenols of the aqueous extract (V. Rodov, Y. Vinokur, N. Gogia, and I. Chkhikvishvili, "Hydrophilic and lipophilic antioxidant capacities of Georgian spices for meat and their possible health implications," Georgian Med. News, no. 179, pp. 61-66, February 2010), (I. Samojlik, N. Lakić, N. Mimica-Dukić, K. Daković-Švajcer, and B. Božin, "Antioxidant and hepatoprotective potential of essential oils of coriander (*Coriandrum sativum* L.) and Caraway (*Carum carvi* L.) (Apiaceae)," J. Agric. Food Chem., vol. 58, no. 15, pp. 8848-8853, August 2010). The antioxidant activity of caraway can contribute to protecting the gastric mucosa from the oxidative stress that is created as a result of prolonged contact with acid (A. Altomare, M. P. L. Guarino, S. Cocca, S. Emerenziani, and M. Cicala, "Gastroesophageal reflux disease: Update on inflammation and symptom perception," World J. Gastroenterol., vol. 19, no. 39, pp. 6523-6528, 2013). Prolonged contact of acid with the oesophageal mucosa can contribute to the generation of reactive oxygen species (ROS) and lesions to the mucosa itself. In fact, ROS can compromise the ability of the mucosa to form a barrier against acid and this contributes to the generation of mucosal lesions (S. Kwiecien, K. Jasnos, M. Magierowski, Z. Sliwowski, R. Pajdo, B. Brzozowski, T. Mach, D. Wojcik, and T. Brzozowski, "Lipid peroxidation, reactive oxygen species and antioxidative factors in the pathogenesis of gastric mucosal lesions and mechanism of protection against oxidative stress—induced gastric injury.," J. Physiol. Pharmacol., vol. 65, no. 5, pp. 613-22, 2014). Mucosal damage induces the production of pro-inflammatory cytokines and chemokines by epithelial cells, which evoke and activate the cells of the immune system; the latter further damage the squamous epithelial cells of the oesophagus (R. Tutuian and D. O. Castell, "Review article: Complete gastro-oesophageal reflux monitoring—Combined pH and impedance," Alimentary Pharmacology and Therapeutics, vol. 24, no. SUPPL. 2. pp. 27-37, September-2006).

In several clinical studies, some herbal preparations containing caraway showed to be effective in reducing the symptoms associated with dyspepsia (Thompson, J. Coon, and E. Ernst, "Systematic review: herbal medicinal products for non-ulcer dyspepsia," Aliment. Pharmacol. Ther., vol. 9, no. Table 1, pp. 1689-1699, 2002).

An important pharmacological effect of *Carum carvi* consists in increasing intestinal motility: this effect should increase the rate of gastric emptying, thus reducing the symptoms associated with dyspepsia and reducing the accumulation of gas in the intestine, with a consequent reduction in the entity of meteorism. In a randomised, placebo-controlled clinical study, the effect of caraway on intestinal motility in women undergoing a caesarean section was assessed (S. S. Yosefi, O. Sadeghpour, F. Sohrabvand, Z. Atarod, M. Askarfarashah, T. R. Ateni, N. H. Yekta, and Department, "Effectiveness of *Carum carvi* on early return of bowel motility after caesarean section," Eur. J. Exp. Biol., vol. 4, no. 3, pp. 258-262, 2014). The women were divided into 2 groups: 2 g of caraway were administered to the first group 8 hours before the surgical intervention and 8 hours and 30 minutes after the intervention, while a placebo was administered to the second group. The time it took to hear the first peristaltic sound after the intervention was significantly shorter in group treated with caraway: 10.0±2.03 hours versus 19.28±3.95 hours (p=0.001) (S. S. Yosefi, O. Sadeghpour, F. Sohrabvand, Z. Atarod, M. Askarfarashah, T. R. Ateni, N. H. Yekta, and Department, "Effectiveness of *Carum carvi* on early return of bowel motility after caesarean section," Eur. J. Exp. Biol., vol. 4, no. 3, pp. 258-262, 2014).

In a study carried out on 12 intestinal bacteria, it was demonstrated that caraway extract has an ability to inhibit the growth of potentially pathogenic bacteria in a selective manner, preserving the bacteria that could have a beneficial effect at the intestinal level (J. A. Hawrelak, T. Cattley, and S. R. Myers, "Essential oils in the treatment of intestinal dysbiosis: A preliminary in vitro study," Altern. Med. Rev., vol. 14, no. 4, pp. 380-384, December 2009). The bacteria mainly sensitive to caraway extract are *Bacterioides fragilis, Clostridium perfringens* and *Clostridium difficile*, which could lead to the occurrence of gastrointestinal problems, including flatulence, bloating, abdominal pain and diarrhoea (J. A. Hawrelak, T. Cattley, and S. R. Myers, "Essential oils in the treatment of intestinal dysbiosis: A preliminary in vitro study," Altern. Med. Rev., vol. 14, no. 4, pp. 380-384, December 2009). The ability of caraway to prevent dysbiosis justifies the traditional use of this plant in the treatment of intestinal disorders.

In a double-blind, placebo-controlled clinical study conducted by May et al. on 96 patients with functional dyspepsia, an assessment was made of the efficacy of a formulation containing peppermint oil (180 mg/die) and caraway oil (100 mg/die) (B. May, S. Kohler, and B. Schneider, "Efficacy and tolerability of a fixed combination of peppermint oil and caraway oil in patients suffering from functional dyspepsia," Aliment. Pharmacol. Ther., vol. 14, no. 12, pp. 1671-1677, December 2000). After 4 weeks of treatment, it was found that there were statistically significant differences in the reduction of the intensity of gastric pain (40% vs 22%, p<0.001) and in the reduction of the sensation of pressure, heaviness and bloating (43.5% vs 22.3%, p<0.001) (B. May, S. Kohler, and B. Schneider, "Efficacy and tolerability of a fixed combination of peppermint oil and caraway oil in patients suffering from functional dyspepsia," Aliment. Pharmacol. Ther., vol. 14, no. 12, pp. 1671-1677, December 2000).

The antispasmodic action of caraway extract is due mainly to its inhibitory action against smooth muscle contractions induced by spasmogens, acetylcholine and histamine [(M. K. Al-Essa, Y. A. Shafagoj, F. I. Mohammed, and F. U. Afifi, "Relaxant effect of ethanol extract of *Carum carvi* on dispersed intestinal smooth muscle cells of the guinea pig", Pharm. Biol., vol. 48, no. 1, pp. 76-80, January 2010), (H. Forster, H. Niklas, and S. Lutz, "Antispasmodic Effects of Some Medicinal Plants," Planta Med., vol. 40, no. 12, pp. 309-319, December 1980)]. It is believed that this action may explain the beneficial effect of caraway which leads to a reduction in the gastrointestinal symptoms associated with dyspepsia (R. G. Hall, H. Thompson, and A. Strother, "Effects of orally administered activated charcoal on intestinal gas.," Am. J. Gastroenterol., vol. 75, no. 3, pp. 192-6, March 1981).

Caraway extracts have shown dose-dependent antiulcerogenic activity against gastric ulcers induced by indomethacin, with an inhibition of leukotriene synthesis and an increased mucus secretion and production of prostaglandin $E_2$. The antiulcerogenic activity, also confirmed by histological examinations, would seem to be due to the polyphenols contained in the aqueous extract (M. T. Khayyal, M. a El-Ghazaly, S. a Kenawy, M. Seif-el-Nasr, L. G. Mahran, Y. a Kafafi, and S. N. Okpanyi, "Antiulcerogenic effect of some gastrointestinally acting plant extracts and their combination.," Arzneimittelforschung., vol. 51, no. 7, pp. 545-553, December 2001).

In the context of the present invention, the dry extract of *Carum carvi* is also indicated as "*Carum carvi*".

Papain

*Carica papaya* belongs to the small family Caricaceae (K. L. Krishna, M. Paridhavi, and J. A. Patel, "Review on nutritional, medicinal and pharmacological properties of papaya (*Carica papaya* linn.)," Indian J. Nat. Prod. Resour., vol. 7, no. 4, pp. 364-373, 2008)]. The fruit, leaves and latex extracted from the fruit are widely used for their different pharmacological properties. The main chemical compound extracted from the fruit is papain, a proteolytic enzyme used as an active ingredient and as a reactive agent in the food and leather industries (K. L. Krishna, M. Paridhavi, and J. A. Patel, "Review on nutritional, medicinal and pharmacological properties of papaya (*Carica papaya* linn.)," Indian J. Nat. Prod. Resour., vol. 7, no. 4, pp. 364-373, 2008). Several other chemical compounds besides papain are present in C.

papaya extract, such as vitamins, proteins, fibres, carbohydrates, minerals, carpain, carposide and the enzyme myrosin.

Papain is a cysteine-protease and belongs to a family of proteins endowed with various activities, including endopeptidase, aminopeptidase, and dipeptidyl peptidase (N. D. Rawlings and A. J. Barrett, "Families of cysteine peptidases," Methods Enzymol., vol. 244, pp. 461-485, 1994).

Within the active site of the enzyme there are 3 amino acid residues, Cys-25, Asn-175 and His-159, which constitute the catalytic triad. Asn-175 modifies the orientation of the imidazole ring of His-159, which serves to deprotonate the cysteine Cys-25: in this manner, a powerful nucleophile is formed which is capable of attaching the peptide bond and forming an intermediate thioether, which, in turn, is attached by a molecule of water, bringing the hydrolysis reaction to an end.

Papain is not endowed with highly selective action, though the hydrolysis catalysed by this enzyme occurs preferentially at the level of a peptide bond between a hydrophobic amino acid residue (Ala, Val, Leu, Ile, Phe, Trp, Tyr) and an arginine or lysine residue (Sigma-Aldrich, "Selective proteolytic enzymes: Papain," 2015. [Online]. Available: http://www.sigmaaldrich.com/life-science/biochemicals/biochemical-products.html?TableP-age=16410606).

In the context of the present invention, papain (CAS N. 9001-73-4) preferably has an activity greater than or equal to 2.5 FIP UI/mg (determinable, for example, with the method of Lauwers, A.; Scharpé, S.: Pharmaceutical Enzymes, drugs and pharmaceutical sciences., Volume 84, Marcel Dekker, Inc., New York-Basel-Hong Kong, 1997).

The use of this enzyme in our formulation is justified by its ability to hydrolyse the peptide bonds of the proteins taken in through the diet. This should enable a higher rate of digestion and, consequently, a higher rate of gastric emptying. Though there exist no studies in the literature on the increase in the rate of gastric emptying following the administration of papain, there are different studies which demonstrate the same activity on the part of actinidin, another cysteine-protease isolated from kiwifruit (C. A. Montoya, S. M. Rutherfurd, T. D. Olson, A. S. Purba, L. N. Drummond, M. J. Boland, and P. J. Moughan, "Actinidin from kiwifruit (*Actinidia deliciosa* cv. Hayward) increases the digestion and rate of gastric emptying of meat proteins in the growing pig," Br. J. Nutr., vol. 111, no. 6, pp. 957-67, March 2014)]. Given the similarity between the two enzymes, it is probable that both are capable of contributing to increasing the rate of digestion of the proteins taken in through the diet. This should lead to fewer problems of flatulence, by preventing putrefactive bacterial flora from fermenting proteins that are taken in through the diet and not completely hydrolysed.

α-Galactosidase

α-galactosidase is an enzyme produced by fungi of the genus *Aspergillus*, in particular *Aspergillus nigrum*. This enzyme is a homodimeric protein capable of hydrolysing the α-galactoside of disaccharides, oligosaccharides, polysaccharides and glycoproteins (M. Hillilä, M. A. Farkkilä, T. Sipponen, J. Rajala, and J. Koskenpato, "Does oral α-galactosidase relieve irritable bowel symptoms?" Scand. J. Gastroenterol., vol. 5521, no. August 2015, pp. 1-6, 2015).

An excessive dietary intake of oligosaccharides, disaccharides and fermentable polyols can lead to the formation of an excessive amount of gas due to the fermentation of these compounds by intestinal bacterial flora (D. K. Ong, S. B. Mitchell, J. S. Barrett, S. J. Shepherd, P. M. Irving, J. R. Biesiekierski, S. Smith, P. R. Gibson, and J. G. Muir, "Manipulation of dietary short chain carbohydrates alters the pattern of gas production and genesis of symptoms in irritable bowel syndrome," J. Gastroenterol. Hepatol., vol. 25, no. 8, pp. 1366-1373, February 2010). Fermentation by bacteria in the intestine is a physiological process which leads to the production of inert gases such as carbon dioxide, methane and hydrogen.

Many foods consumed in the diet, such as cereals, legumes, fruit and vegetables, contain oligosaccharides such as raffinose, stachyose and verbascose, which have glycosidic bonds in the a configuration. These compounds cannot be hydrolysed by the hydrolase produced by humans. Given that, due to their excessive molecular weight and excessive lipophilicity, these molecules are not absorbed in significant amounts in the intestine, they act as a substrate for fermentation by bacteria.

It has been found that the administration of α-galactosidase can thus constitute a valid approach for reducing the formation of gas: hydrolysis of α-galactosides should lead to the formation of monosaccharides absorbable in the intestine, thus eliminating the substrate for bacterial fermentation, which should result in a reduced formation of intestinal gas.

In fact, there exist numerous studies that support this assumption. The efficacy of α-galactosidase was demonstrated in a randomised, cross-over clinical study conducted on healthy volunteers. After the administration of a dish containing beans, in fact, a statistically significant ($p<0.04$) reduction in the average number of episodes of flatulence was observed 5 hours after the meal in the group treated with α-galactosidase compared to the placebo group (T. G. Ganiats, W. A. Norcross, A. L. Halverson, P. A. Burford, and L. A. Palinkas, "Does Beano prevent gas? A double-blind crossover study of oral alpha-galactosidase to treat dietary oligosaccharide intolerance.," J. Fam. Pract., vol. 39, no. 5, pp. 441-445, November 1994).

In another randomised, double-blind, placebo-controlled clinical study, statistically significant reductions in breath hydrogen excretion and the severity of flatulence were observed following the administration of a meal rich in fermentable carbohydrates (420 g of beans) (M. di Stefano, E. Miceli, S. Gotti, A. Missanelli, S. Mazzocchi, and G. R. Corazza, "The effect of oral alpha-galactosidase on intestinal gas production and gas-related symptoms," Dig. Dis. Sci., vol. 52, no. 1, pp. 78-83, January 2007). 300 or 1200 GalU of α-galactosidase or a placebo were administered to healthy volunteers and various parameters associated with the production of gas were evaluated over the following 8 hours. A statistically significant reduction in the amount of breath hydrogen was observed in the volunteers treated with 1200 GalU of α-galactosidase, and a reduction in the symptoms of flatulence was observed in all volunteers, though it was statistically significant only in patients treated with 300 and 1200 GalU of α-galactosidase (M. di Stefano, E. Miceli, S. Gotti, A. Missanelli, S. Mazzocchi, and G. R. Corazza, "The effect of oral alpha-galactosidase on intestinal gas production and gas-related symptoms," Dig. Dis. Sci., vol. 52, no. 1, pp. 78-83, January 2007).

In another randomised, double-blind, placebo-controlled clinical study, the action of α-galactosidase in the treatment of the symptoms of irritable bowel syndrome was evaluated (M. Hillilä, M. A. Färkkilä, T. Sipponen, J. Rajala, and J. Koskenpato, "Does oral α-galactosidase relieve irritable bowel symptoms?," Scand. J. Gastroenterol., vol. 5521, no. August 2015, pp. 1-6, 2015). The patients participating in the study were randomly assigned to one of two groups of 62 patients each. The first received a dose of 400 GalU of α-galactosidase 3 times a day and the second a placebo 3 times a day. A reduction in the IBS-Symptom Severity Score (IBS-SSS) was observed in both groups: 67 points in the group treated with α-galactosidase and 47.2 points in the placebo group. The percentage of patients who responded positively to the therapy was significantly higher (p=0.028) in the group treated with α-galactosidase compared to the placebo group 4 weeks after the treatment (M. Hillilä, M. A. Färkkilä, T. Sipponen, J. Rajala, and J. Koskenpato, "Does oral α-galactosidase relieve irritable bowel symptoms?," Scand. J. Gastroenterol., vol. 5521, no. August 2015, pp. 1-6, 2015).

β-Galactosidase

β-galactosidase is a glycosidic hydrolase that catalyses the hydrolysis reaction of β-galactosides into the monosaccharides making them up.

It is a fundamental enzyme for human beings and a deficiency thereof is associated with malabsorption of lactose, which is not broken down into the monosaccharides glucose and galactose (Y. Wang, C. B. Harvey, E. J. Hollox, A. D. Phillips, M. Poulter, P. Clay, J. A. Walker-Smith, and D. M. Swallow, "The genetically programmed down-regulation of lactase in children," Gastroenterology, vol. 114, no. 6, pp. 1230-1236, June 1998). It is present in infants in a high concentration, but with aging there is a progressive, genetically programmed down-regulation of its activity in most of the world population (E. Gudmand-Høyer, "The clinical significance of disaccharide maldigestion," in American Journal of Clinical Nutrition, 1994, vol. 59, no. 3 SUPPL., p. 735S-741S). The deficiency of this enzyme has a high incidence, which reaches 70% in the population of southern Italy (M. Montalto, G. Nucera, L. Santoro, V. Curigliano, M. Vastola, M. Covino, L. Cuoco, R. Manna, a Gasbarrini, and G. Gasbarrini, "Effect of exogenous beta-galactosidase in patients with lactose malabsorption and intolerance: a crossover double-blind placebo-controlled study.," Eur. J. Clin. Nutr., vol. 59, no. 4, pp. 489-493, 2005).

The non-hydrolysis of lactose may lead to gastrointestinal problems like bloating, abdominal pain and diarrhoea, a condition known as "lactose intolerance".

A possible strategy for avoiding this disorder consists in avoiding the consumption of milk and dairy products. However, this approach leads to a reduced dietary intake of calcium, phosphorous and vitamins, which in the long term can cause osteopenia and osteoporosis.

A more promising approach consists in the administration of exogenous β-galactosidase. This leads to an increase in the breakdown of the lactose taken in through the diet, thus reducing the formation of gas by intestinal bacterial flora, as well as drawing water by osmosis, with a consequent reduction in diarrhoea. There are a number of clinical studies that support the effectiveness of this approach.

In a clinical study conducted by Montalto et al., the action of the β-galactosidase was assessed in patients with lactose intolerance who received a dose of 400 mL of partly skimmed milk containing about 20 g of lactose (M. de Vrese, C. Laue, B. Offick, E. Soeth, F. Repenning, A. Thoβ, and J. Schrezenmeir, "A combination of acid lactase from *Aspergillus oryzae* and yogurt bacteria improves lactose digestion in lactose maldigesters synergistically: A randomized, controlled, double-blind cross-over trial," Clin. Nutr., vol. 34, no. 3, pp. 394-399, 2015). The patients participating in the study were divided into 3 groups: group A received milk to which 3000 U of lactase were added 10 hours prior to administration; group B received milk to which 6000 U of lactase were added 5 minutes prior to ingestion; group C received milk with the addition of aspartame, a sweetener used to impart a sweetness to the milk similar to that of the milk of the first 2 groups. Samples of expired air were taken after fasting and at 30-minute intervals for 4 hours following ingestion of milk. A statistically significant reduction (p<0.001) in the hydrogen concentration was found: 77% in group A (12.07±7.8 p.p.m.) and 73% in group B (13.97±7.99 p.p.m.), respectively, compared to the placebo (51.46±16.12 p.p.m.). The cumulative quantity of expired hydrogen was also significantly lower in groups A and B versus group C (M. de Vrese, C. Laue, B. Offick, E. Soeth, F. Repenning, A. Thoβ, and J. Schrezenmeir, "A combination of acid lactase from *Aspergillus oryzae* and yogurt bacteria improves lactose digestion in lactose maldigesters synergistically: A randomized, controlled, double-blind cross-over trial," Clin. Nutr., vol. 34, no. 3, pp. 394-399, 2015).

In another study, it was demonstrated that the association of lactase and probiotic bacteria present in the yogurt was effective in reducing the symptoms of lactose intolerance.

The present invention makes it possible to obtain, simultaneously:

Prokinetic effect, i.e. selective stimulation of the gastrointestinal motor function;

Adsorption of intestinal gases;

Reduction in the formation of gas.

*Carum carvi* extract exhibits numerous activities that are useful in the treatment of gastrointestinal disorders. One of the most important among them is probably the prokinetic activity, i.e. selective stimulation of the gastrointestinal motor function, which can increase the rate of gastric emptying, thus contributing to reducing one of the possible causes of dyspepsia and other gastrointestinal disorders.

Papain is an aspecific proteolytic enzyme that helps endogenous protease to hydrolyse the proteins taken in through the diet, thus contributing to increasing the rate of gastric emptying, which is correlated to the amount of proteins present in the stomach.

The activated charcoal present in the formulation, thanks to its gas adsorption capacity, mechanically reduces the volume of the gas present inside the intestine. Preferably, but without limitations, the activated charcoal in the composition according to the present invention is a food grade vegetable charcoal with a density between 500 and 700 kg/m$^3$, and/or with iodine absorption of about 1000 mg/g or greater than 1000 mg/g.

Preferably, the composition according to the invention comprises, in addition to a) activated charcoal, b) *Carum carvi* extract and c) papain, extracted from *Carica papaya*, at least one between:

d. α-galactosidase;

e. β-galactosidase.

α-galactosidase, optionally present in the composition according to the present invention, hydrolyses α-galactosides into the respective monomers, which are absorbed in the intestine. This prevents these compounds from being fermented by the intestinal bacterial flora, thus reducing the quantity of intestinal gases. In the context of the present invention, preferably, but without limitation, the α-galactosidase derives from the fermentation of a strain of *Aspergillus niger* and has an activity equal to or greater than 30000 galU/g (measured by means of a spectrophotometric method based on how much 4-nitrophenol is released in 15 minutes by hydrolysis of p-nitrophenyl-alpha-D-galactopyranoside).

β-galactosidase (lactase), thanks to its ability to hydrolyse β-galactosides, lactose in particular, reduces the fermentation of these compounds taken in through the diet, thus further reducing the formation of intestinal gases. In the context of the present invention, preferably, but without limitation, β-galactosidase derives from the fermentation of a strain of *Aspergillus oryzae* and has an activity equal to or greater than 100000 FCC (Food Chemical Codex) ALU/g (measured by means of a spectrophotometric method based on how much 4-nitrophenol is released in 15 minutes by hydrolysis of o-nitrophenyl-β-D-galactopyranoside at 37° C. at pH 4.5, reference: analytical method specified in the Compendium of monographs FAO JECFA 1956-2005 volume 4, ISSN 1817-7077 http://www.fao.org/docrep/009/a0691e/A0691E07.htm).

Papain is an aspecific proteolytic enzyme that helps endogeneous protease to hydrolyse the proteins taken in through the diet, thus preventing them from being a substrate for fermentation by putrefactive intestinal flora.

*Carum carvi*, by virtue of its prokinetic activity, can lead to a reduction in the accumulation of gas inside the intestine, with a consequent reduction in bloating and meteorism.

The synergistic combination of the prokinetic effect and the effect of increasing proteolysis leads to an increase in the rate of gastric emptying, with a reduction in dyspepsia and other gastrointestinal disorders. The combination of the effect of intestinal gas adsorption, the effect of reducing the production of gas by the bacterial flora and the prokinetic effect makes it possible to have a reduction in the volume of gas present in the intestine, with a consequent reduction in the flatulence, meteorism and abdominal bloating which characterise many gastrointestinal disorders.

A considerable synergy has been observed between the components of the mixture according to the present invention, i.e. the increase in the rate of gastric emptying and reduction in the volume of gas present in the intestine observed after administration of the mixture are greater than the simple sum of the effects obtained by administering each of the components.

The composition according to the present invention is preferably for use in the curative or preventive treatment of disorders selected from among dyspepsia, pyrosis and/or gastroesophageal reflux, meteorism and/or flatulence, diarrhoea and irritable bowel syndrome; preferably meteorism, flatulence and/or diarrhoea.

It remains understood that the subject matter of the present invention relates to the use of activated charcoal, *Carum carvi* extract, papain and, if present, α-galactosidase and β-galactosidase in the curative and/or preventive treatment of the symptoms and gastrointestinal disorders associated with the presence of gas in the intestine, both when said active ingredients are administered simultaneously, i.e. in a mixture in the same composition, and when they are administered to a subject, in any order, in a sequence over a short period of time in two or more distinct compositions.

Description of the Formula

As previously mentioned, in the present invention the synergistic action takes place between activated charcoal, *Carum carvi* extract, papain and, if present, α-galactosidase and β-galactosidase. The greatest synergy is obtained when activated charcoal is present in an amount comprised from 100 mg to 5000 mg, *Carum carvi* extract is present in an amount comprised from 30 mg to 300 mg, papain, extracted from the plant *Carica papaya* L., is present in an amount comprised from 5 mg to 100 mg and, if present, α-galactosidase is present in an amount comprised from 5 mg to 100 mg and 3-galactosidase is present in an amount comprised from 5 mg to 100 mg.

Preferably, in the composition according to the present invention, activated charcoal is present in an amount comprised from 100 mg to 5000 mg, more preferably from 500 to 3000 mg or 1000 to 2000 mg, *Carum carvi* extract is present in an amount comprised from 30 mg to 300 mg, preferably from 50 to 250 mg or 100 to 200 mg, papain, extracted from the plant *Carica papaya* L., is present in an amount comprised from 5 mg to 100 mg, more preferably from 20 to 50 mg and, if present, α-galactosidase is present in an amount comprised from 5 mg to 100 mg, more preferably from 10 to 75 mg or 30 to 50 mg and/or β-galactosidase is present in an amount comprised from 5 mg to 100 mg, more preferably from 20 to 50 mg.

The composition according to the invention is preferably in a form suitable for oral administration, as known to the person skilled in the art of food, pharmaceutical and/or nutraceutical formulations, more preferably in solid form, optionally having a gastro-resistant coating, such as a tablet, a hard or soft capsule, a powder, or a granulate, optionally to be taken after dissolution or suspension in water, or in liquid or semi-liquid form, such as a syrup, a solution, a suspension or a gel.

The composition according to the present invention may comprise, in addition to said mixture of activated charcoal, *Carum carvi* extract, papain and, if present, α-galactosidase and β-galactosidase, at least one other biologically active substance, such as an active pharmaceutical ingredient, a vegetable extract, a probiotic bacterium and/or one or more vitamins. Non-limiting examples of such active ingredients are the ones known for having a curative and/or preventive action against gastrointestinal disorders. Non-limiting examples of the vegetable extracts are extracts of *Pimpinella anisum* L., *Matricaria chamomilla* L., *Foeniculum vulgare* Mill. and, in general, of all medicinal plants known for having a curative and/or preventive action against gastrointestinal disorders. Non-limiting examples of probiotic bacteria are viable or non-viable strains of the genus *Lactobacillus* or *Bifidobacterium*. Non-limiting examples of vitamins are group B vitamins, vitamin C, vitamin D, vitamin E and vitamin K.

The composition according to the invention can further comprise, in addition to said mixture of activated charcoal, *Carum carvi* extract, papain and, if present, α-galactosidase and β-galactosidase, and, optionally, at least one other biologically active substance, at least one pharmaceutically acceptable or food grade excipient and/or technological additive. Non-limiting examples of such ingredients, as known to the person skilled in the art of pharmaceutical, nutraceutical or food formulations, are diluent excipients, absorbents, adsorbents, lubricants, glidants, colourants, surfactants, antioxidants, sweeteners, flavourings, binders, disintegrating agents, plasticisers, thickeners, emulsifiers, humectants, wetting agents, preservatives, chelating agents and others known to the person skilled in the art.

Advantageously, the composition according to the invention, in the form of a composition for oral use, is well tolerated when used on its own or in association/combination with pharmacological and/or surgical treatments.

The subject matter of the present invention further relates to the use of a composition comprising a mixture which comprises, or, alternatively, consists of activated charcoal, *Carum carvi* extract, papain and, if present, α-galactosidase, β-galactosidase to increase the rate of gastric emptying and/or for the prevention of the formation or the elimination of excess gas in the intestine.

Preferred embodiments of the present invention are illustrated below, without any intention of limiting the scope thereof.

Some preferred, but non-limiting examples of the formulation are the following:

EXAMPLE 1

| Active ingredient | Daily dose |
|---|---|
| Activated charcoal | 2000 mg |
| Carum carvi d.e. (dry extract) | 120 mg |
| Papain | 20 mg |

EXAMPLE 2

| Active ingredient | Daily dose |
|---|---|
| Activated charcoal | 2000 mg |
| Carum carvi d.e. | 120 mg |
| α-galactosidase | 20 mg |
| β-galactosidase | 20 mg |
| Papain | 20 mg |

EXAMPLE 3

| Active ingredient | Daily dose |
|---|---|
| Activated charcoal | 500 mg |
| Carum carvi d.e. | 120 mg |
| β-galactosidase | 20 mg |
| Papain | 20 mg |
| α-galactosidase | 10 mg |

Experimental Part

Studies conducted on the composition of the present invention for the treatment of gastrointestinal disorders.

An assessment was made of the effect of a composition of the present invention and of the individual constituents (in order to observe the synergistic effect between the individual components) (i) on the rate of gastric emptying.

Components:

Papain (CAS N. 9001-73-4): activity greater than or equal to 2.5 FIP UI/mg (determinable, for example, with the method of Lauwers, A.; Scharpé, S.: Pharmaceutical Enzymes, drugs and pharmaceutical sciences., Volume 84, Marcel Dekker, Inc., New York-Basel-Hong Kong, 1997);

Carum carvi dry extract obtained by aqueous extraction of Carum carvi, in a mixture with maize maltodextrin, in an E/D (Extract/Drug, i.e. plant extract) ratio of 1:4.

Vegetable charcoal FCC (food grade from coconut) with a density approx. 510 kg/m$^3$, iodine absorption approx. 1000 mg/g.

Animals

Male mice of the ICR strain, weighing 20-25 g, were used. The animals were housed in temperature-controlled rooms (temperature of 23±2° C., humidity of 50±2%, 12-hour light-dark cycles) and had free access to water and food, consisting of a standard diet. All experiments were performed in observance of Legislative Decree no. 116 of 27 Jan. 1992 and according to the guidelines of the Council of the European Union (86/609/EEC and 2010/63/EU).

Gastric Emptying

Gastric emptying is evaluated with the method described by Smits and Lefebvre [Smits G J, Lefebvre R A. Influence of aging on gastric emptying of liquids, small intestine transit, and fecal output in rats. Exp Gerontol. 1996; 31(5): 589-96]. For the purpose of determining gastric emptying, a marker was administered to the mice (0.2 mL/mouse of a suspension containing 50 mg of phenol red in 100 mL 1.5% carboxymethylcellulose). After twenty minutes, the animals were sacrificed in an atmosphere saturated with $CO_2$ and the stomach was removed. The stomach was subsequently positioned inside a test tube containing 4 mL of physiological solution; after 20 seconds of shaking, 2 mL of NaOH 1 M were added to each test tube in order to develop the maximum colour intensity. Spectrophotometric analysis (performed at a wavelength of 560 nm) was conducted on 1 mL of this solution. Finally, the percentage of gastric emptying was calculated.

Diarrhoea

In the following tests, the effect of two formulations and their individual constituents was evaluated in order to determine a possible synergistic effect among the individual components on diarrhoea induced by castor oil.

Materials and Methods

Animals

Male mice of the ICR strain supplied by the company Charles River and weighing 20-25 g were used. The animals were housed in temperature-controlled rooms (temperature of 23±2° C., humidity of 50±2%, 12-hour light-dark cycles) and had free access to water and food, consisting of a standard diet supplied by the company Mucedola Mangimi (Settimo Milanese, Italy). All experiments were performed in observance of Legislative Decree no. 116 of 27 Jan. 1992 and according to the guidelines of the Council of the European Union (86/609/EEC and 2010/63/EU).

Diarrhoea Induced by Castor Oil

The technique of Borrelli et al. (Borrelli F, Capasso F, Capasso R, Ascione V, Aviello G, Longo R, Izzo A A (2006). "*Effect of Boswellia serrata on intestinal motility in rodents: inhibition of diarrhoea without constipation*" Br J Pharmacol 148:553-560) was used. In practical terms, the mice were fasted for a period of 12 hours and then isolated in individual cages provided with a mesh on the bottom, set 5 cm above a sheet of absorbent paper. This enabled inspection of the excreted faeces. 30 minutes after administration of the samples to be tested, the animals received 0.2 ml of castor oil by means of a gastric probe. The diarrhoea was evaluated 15 minutes after the administration of the cathartic agent and every 15 minutes until the second hour. The results were expressed as the percentage of mice that exhibited diarrhoea at the second hour.

Pharmacological Treatment

The mice were divided into groups of 10-12 animals and treated with the following substances/extracts: activated charcoal, Carum carvi, papain, α-galactosidase and β-galactosidase. Three/four doses were used for each substance in order to identify the submaximal dose (dose which induces a significant, but not maximal, effect), which was subsequently used to evaluate the effect of the formulations. The doses used were selected considering the doses used in humans and the doses used in preclinical studies reported in the literature.

Two formulations (according to the invention) were evaluated, consisting, respectively, of activated charcoal, Carum carvi, papain, α-galactosidase and β-galactosidase (total formulation) and activated charcoal, Carum carvi and papain (partial formulation).

The treatments were carried out orally 30 minutes before the oral administration of castor oil.

Statistical Analysis

The results are expressed as the mean±standard error of the mean (S.E.M.). The difference between two means was evaluated by means of Student's t-test. Analysis of variance was used instead to compare more than two means. A value of $p<0.05$ was considered statistically significant.

Results

Figure 1:
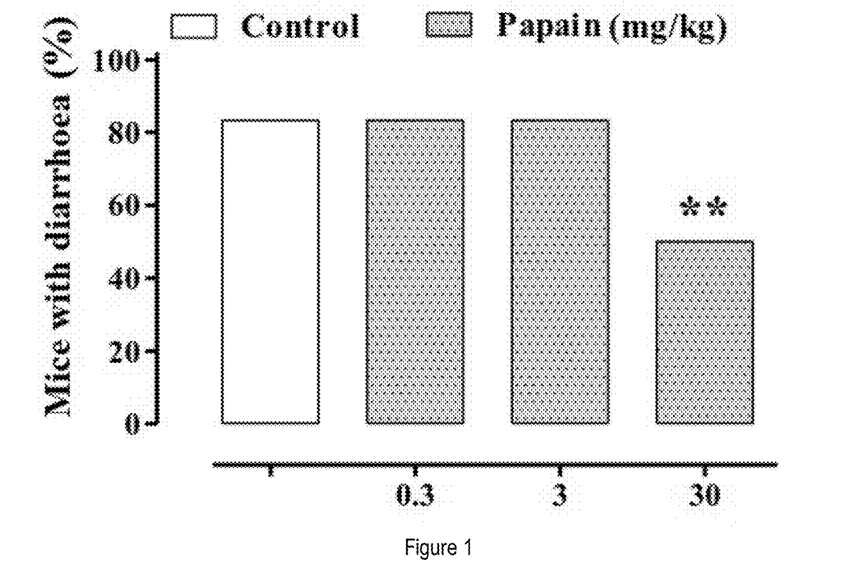

FIG. 1: Effect of papain (0.3-30 mg/kg) on diarrhoea induced by the administration of the cathartic agent, castor oil (0.2 ml/mouse). The effect was evaluated 2 hours after the administration of castor oil. Each bar represents the mean±S.E.M. of 10-12 animals. "p<0.01 vs control.

Figure 2:
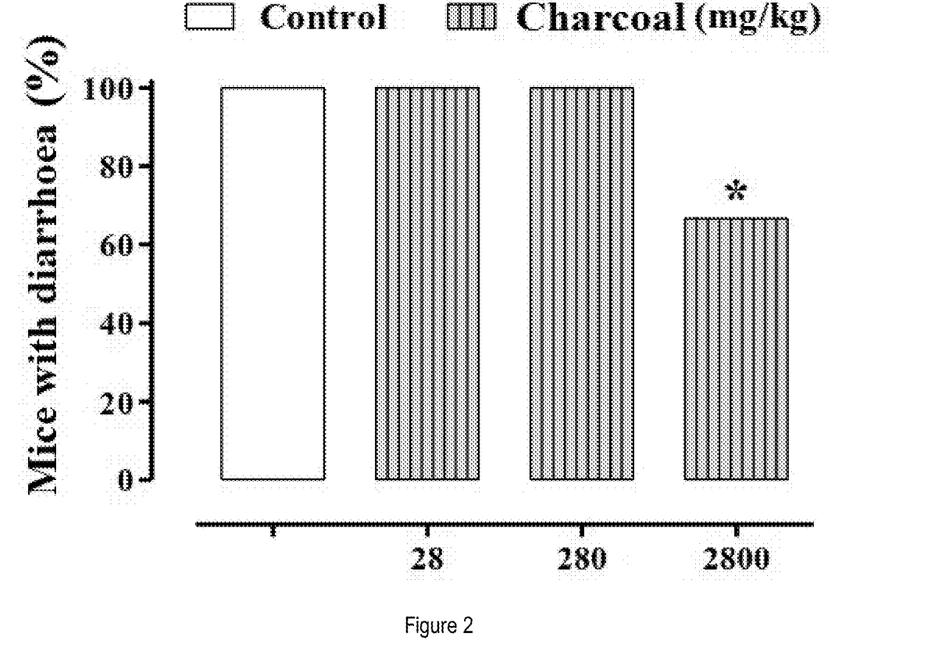

FIG. 2: Effect of the activated charcoal (28-2800 mg/kg) on diarrhoea induced by the administration of the cathartic agent, castor oil (0.2 ml/mouse). The effect was evaluated 2 hours after the administration of castor oil. Each bar represents the mean±S.E.M. of 10-12 animals. *p<0.05 vs control.

Figure 3:
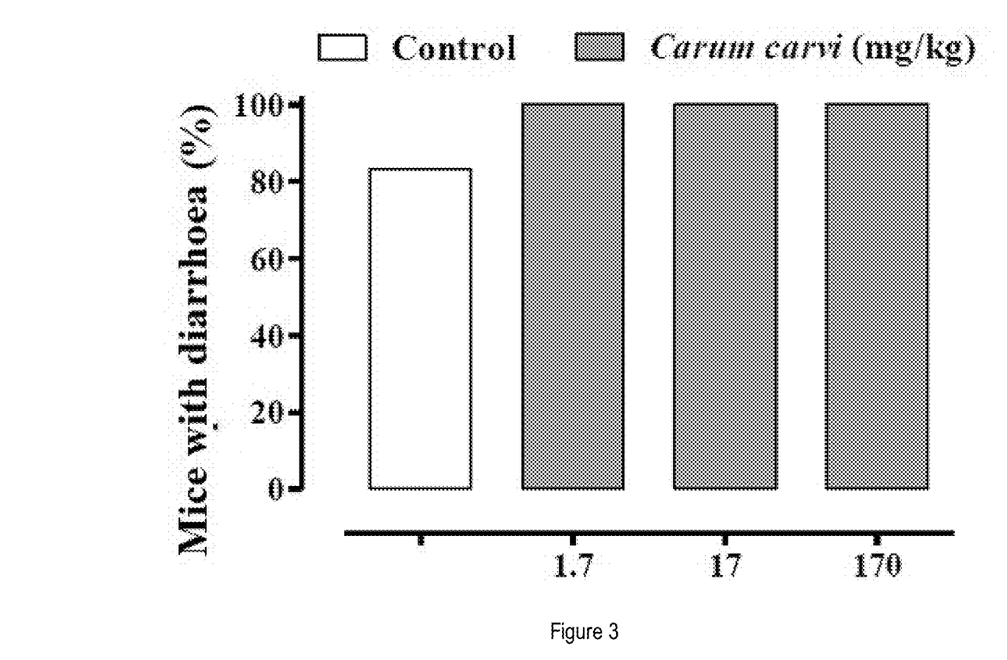

FIG. 3: Effect of Carum carvi (1.7-170 mg/kg) on diarrhoea induced by the administration of the cathartic agent, castor oil (0.2 ml/mouse). The effect was evaluated 2 hours after the administration of castor oil. Each bar represents the mean±S.E.M. of 10-12 animals.

Figure 4:
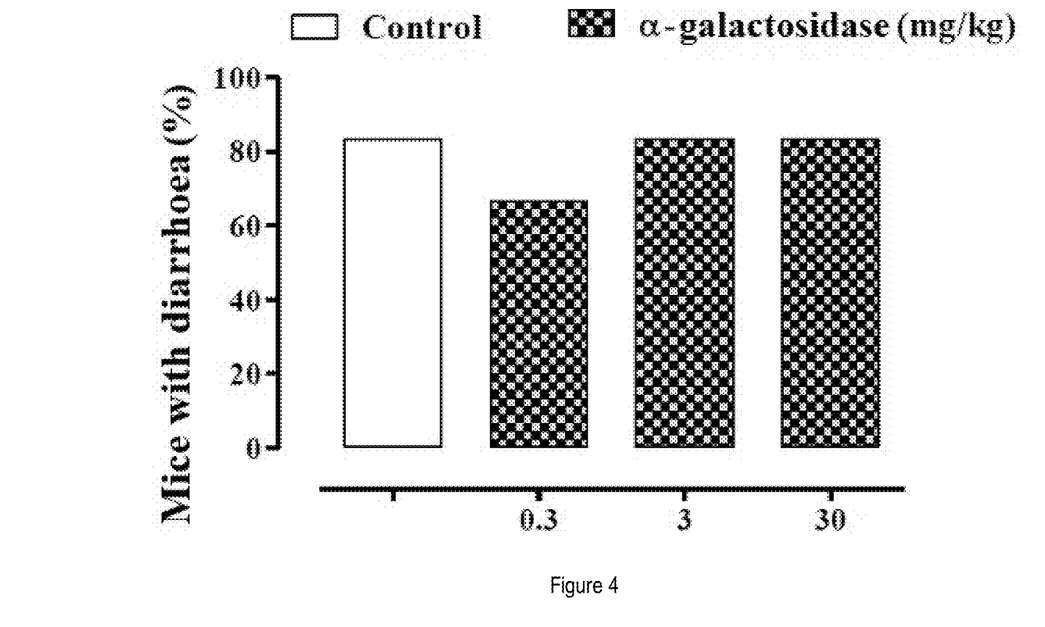

FIG. 4: Effect of α-galactosidase (0.3-30 mg/kg) on diarrhoea induced by the administration of the cathartic agent, castor oil (0.2 ml/mouse). The effect was evaluated 2 hours after the administration of castor oil. Each bar represents the mean±S.E.M. of 10-12 animals.

Figure 5:
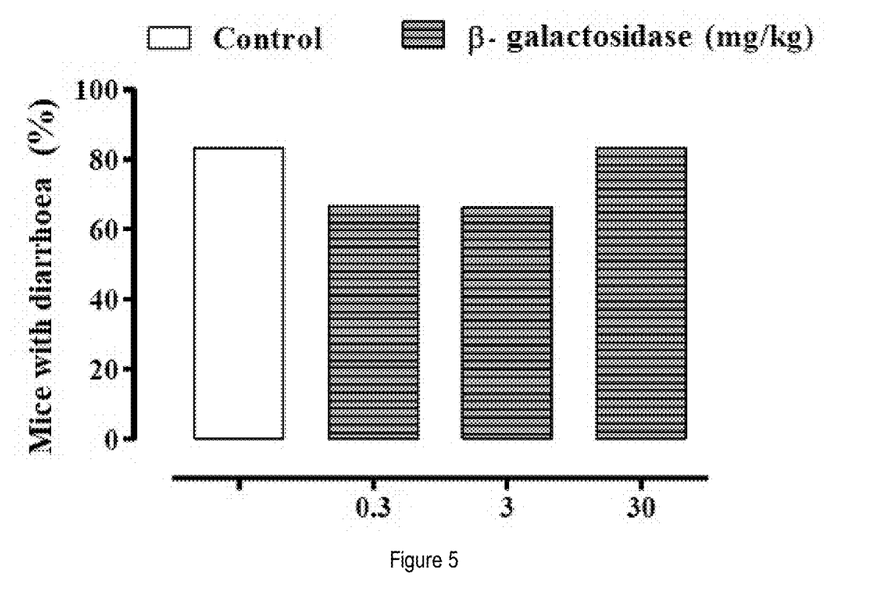

FIG. 5: Effect of β-galactosidase (0.3-30 mg/kg) on diarrhoea induced by the administration of the cathartic agent, castor oil (0.2 ml/mouse). The effect was evaluated 2 hours after the administration of castor oil. Each bar represents the mean±S.E.M. of 10-12 animals.

Figure 6:
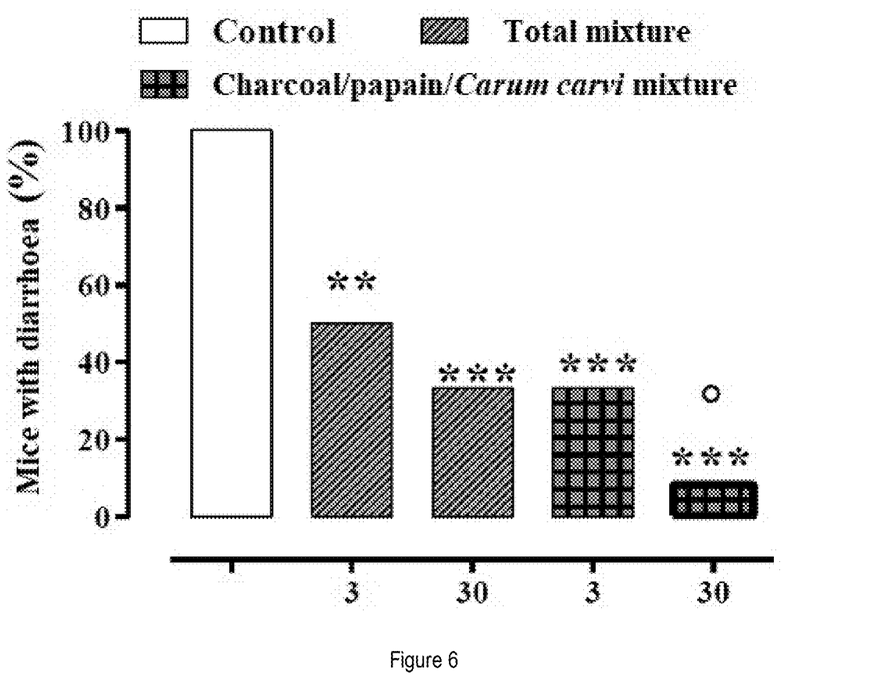

FIG. 6: Effect of the total formulation [obtained from the combination of papain (3 mg/kg), Carum carvi (1.7 mg/kg), α-galactosidase (3 mg/kg) and β-galactosidase (3) and charcoal (280 mg/kg) or papain (30 mg/kg), Carum carvi (17 mg/kg), α-galactosidase (30 mg/kg) β-galactosidase 30 mg/kg) and charcoal (2800 mg/kg)] and of the partial formulation [obtained from the combination of papain (3 mg/kg), Carum carvi (1.7 mg/kg) and charcoal (280 mg/kg) or papain (30 mg/kg), Carum carvi (17 mg/kg) and charcoal (2800 mg/kg)] on diarrhoea induced by the administration of the cathartic agent, castor oil (0.2 ml/mouse). The effect was evaluated 2 hours after the administration of castor oil. Each bar represents the mean±S.E.M. of 10-12 animals. "p<0.01 and ***p<0.001 vs control; ° p<0.01 vs total mixture 30.

Papain (administered orally at the doses comprised between 0.3 and 30 mg/kg) and charcoal (administered orally at the doses comprised between 28 and 2800 mg/kg) significantly reduced diarrhoea 2 hours after the administration of castor oil, the effect being significant at the dose of 30 mg/kg in the case of papain (FIG. 1) and 2800 mg/kg in the case of charcoal (FIG. 2). In contrast, Carum carvi (1.7-170 mg/kg), α-galactosidase (0.3-30 mg/kg) and β-galactosidase (0.3-30 mg/kg), administered orally (at all the doses used) were not capable of modifying the cathartic effect of the castor oil (FIG. 3-5). The total formulation [obtained from the combination of papain (3 and 30 mg/kg), Carum carvi (1.7 and 17 mg/kg), α-galactosidase (3 and 30 mg/kg) β-galactosidase (3 and 30 mg/kg) and charcoal (280 and 2800 mg/kg)] and the partial formulation [obtained from the combination of papain (3 and 30 mg/kg), Carum carvi (1.7 and 17 mg/kg) and charcoal (280 and 2800 mg/kg)], (used at doses that were inactive in themselves) significantly reduced, in a dose-dependent manner, diarrhoea induced by castor oil (FIG. 6). The partial formulation, at the highest dose used (30 mg/kg of papain, 17 mg/kg of Carum carvi extract and 2800 mg/kg of charcoal), was much more active than the total formulation at the same doses of papain, Carum carvi extract and activated charcoal (FIG. 6).

The invention claimed is:

1. A method for treating diarrhoea, or a symptom thereof, in a subject, comprising orally administering to the subject an effective amount of a composition comprising the following components:
   a) 3000 mg-5000 mg activated charcoal;
   b) 30 mg-50 mg Carum carvi extract; and
   c) 20 mg-50 mg papain, extracted from Carica papaya.

2. The method according to claim 1, wherein the composition further comprises:
   d) α-galactosidase;
   e) β-galactosidase; or
   f) α-galactosidase and β-galactosidase.

3. The method according to claim 1, wherein the composition further comprises α-galactosidase is present in an amount from 5 mg to 100 mg or, if present, β-galactosidase is present in an amount from 5 mg to 100 mg, or combinations thereof.

4. The method according to claim 1, wherein the composition is in the form of a tablet, a capsule, a powder, a granulate, a syrup, a solution, a suspension or a gel, each being suitable for oral administration.

5. The method according to claim 1, wherein the composition further comprises at least one pharmaceutically acceptable excipient, food grade excipient or technological additive, or combinations thereof.

* * * * *